US00PP31705P2

(12) United States Plant Patent
Cho

(10) Patent No.: US PP31,705 P2
(45) Date of Patent: Apr. 28, 2020

(54) ***LEUCADENDRON* PLANT NAMED 'HAWAII SUNRISE'**

(50) Latin Name: ***Leucadendron stelligerum* x *discolor***
Varietal Denomination: Hawaii Sunrise

(71) Applicant: University of Hawaii, Honolulu, HI (US)

(72) Inventor: John J. Cho, Kahului, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 16/501,547

(22) Filed: Apr. 29, 2019

(51) Int. Cl.
*A01H 5/02* (2018.01)
*A01H 6/36* (2018.01)

(52) U.S. Cl.
USPC ..... Plt./226

(58) Field of Classification Search
USPC ..... Plt./226
CPC ..... A01H 5/00; A01H 5/02; A01H 6/36
See application file for complete search history.

*Primary Examiner* — June Hwu
(74) *Attorney, Agent, or Firm* — Barbara Campbell; James M. Weatherly; Cochran Freund & Young LLC

(57) ABSTRACT

A new cultivar of *Leucadendron* plant named 'Hawaii Sunrise' that is distinguished by a very compact bushy plant habit with densely packed foliage and many current-season branches which are bright red in color and which bear terminal inflorescences whose bracts are yellow in color with contrasting bright orange-red coloration to their apex and margin. 'Hawaii Sunrise' bears only male flowers which are bright yellow in color.

2 Drawing Sheets

Figure 1:
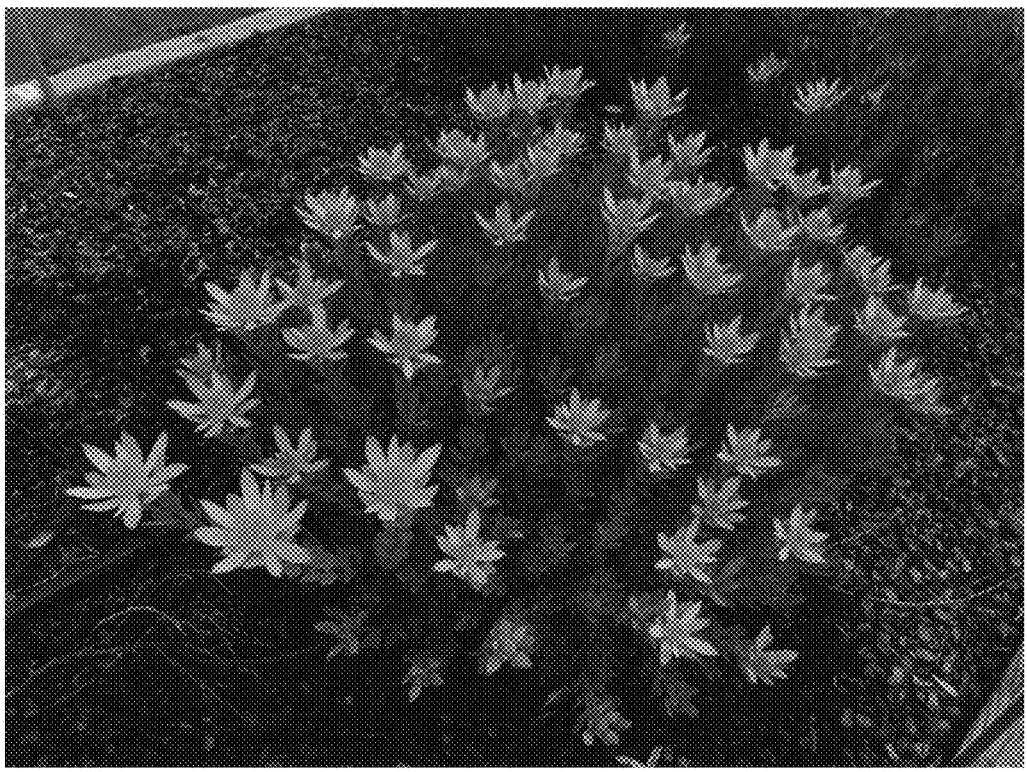

Genus and species: *Leucadendron stelligerum* x *discolor*.
Variety denomination: 'Hawaii Sunrise'.

BACKGROUND OF THE NEW PLANT

The present invention relates to a new variety of *Leucadendron stelligerum* x *discolor*, hereinafter referred to by the cultivar name 'Hawaii Sunrise'. 'Hawaii Sunrise' is a hybrid selection which originated from the inventor's breeding program in Kula, Hi. The genus *Leucadendron* is a member of the Proteaceae or Protea family which is a significant commercial class of Mediterranean plants used as cut flowering stems and ornamental container plants.

The inventor commenced his *Leucadendron* breeding program in 2011. The objective of the breeding program to develop small or dwarf types of protea for the worldwide container ornamental plant market with novel foliage colors, superior growth habits for commercial cultivation and for home gardener use.

In 2012, the inventor carried out controlled pollination between an unnamed and unpatented plant of *Leucadendron discolor* as the male parent and an unnamed and unpatented plants of *Leucadendron stelligerum* as the female parent. 'Hawaii Sunrise' was selected as an individual in spring 2013 for its bright yellow flowers and naturally compact and branching and secondary branching habit.

The inventor first asexually propagated 'Hawaii Sunrise' in May 2014 in Kula, Hi. using semi-ripe tip cuttings. 'Hawaii Sunrise' has been found to remain stable and uniform and to reproduce true to type in successive generations of asexual reproduction. 'Hawaii Sunrise' has not been sold or made publicly available more than one year prior to the filing date of the instant application.

SUMMARY

The following traits have been repeatedly observed and represent the distinguishing characteristics of 'Hawaii Sunrise'. In combination these traits set the new cultivar apart from all others existing varieties of *Leucadendron* known to the inventor. 'Hawaii Sunrise' has not been tested under all possible conditions and phenotypic differences may be observed with variations in environment, climatic, and cultural conditions, however, without any variance in genotype.

1. 'Hawaii Sunrise' exhibits a very compact bushy plant habit.
2. A one-year old plant of 'Hawaii Sunrise' is approximately 30 cm in height and 30 cm in width.
3. A four-year old plant of 'Hawaii Sunrise' is approximately 65 cm in height and 65 cm in width.
4. The foliage of 'Hawaii Sunrise' is densely packed with pairs of leaves every 6 mm.
5. The stems of the current year's growth of 'Hawaii Sunrise' are bright red in color.
6. 'Hawaii Sunrise' branches prolifically once established. 8 to 12 branches are formed each year on the previous year's wood.
7. The terminal inflorescences of 'Hawaii Sunrise' are borne on every current season branch and are very numerous.
8. Each inflorescence of 'Hawaii Sunrise' bears showy bracts which are yellow in color with contrasting bright orange-red coloration to their apex and margin.
9. 'Hawaii Sunrise' bears only male flowers which are bright yellow in color.
10. 'Hawaii Sunrise' prefers humus rich, acid, well-drained medium, which is low in phosphorus.

BRIEF DESCRIPTION OF THE PHOTOGRAPHS

The accompanying drawings illustrate the distinguishing traits of the new *Leucadendron* cultivar 'Hawaii Sunrise'. All plants in the drawings have received one pinch after initial cutting establishment. The plants have been grown without any chemical growth regulators. The drawings were made from digital photographic images. Although colors may appear different from actual colors due to light reflectance, they are as accurate as possible by conventional or digital photography.

FIG. 1 depicts a three-year old plant of 'Hawaii Sunrise' in late March. The plant has been grown outdoors in Oxnard, Calif. At this time of year, the foliage color of 'Hawaii Sunrise' is olive green becoming deep purple towards and at the terminal growth.

Figure 2:
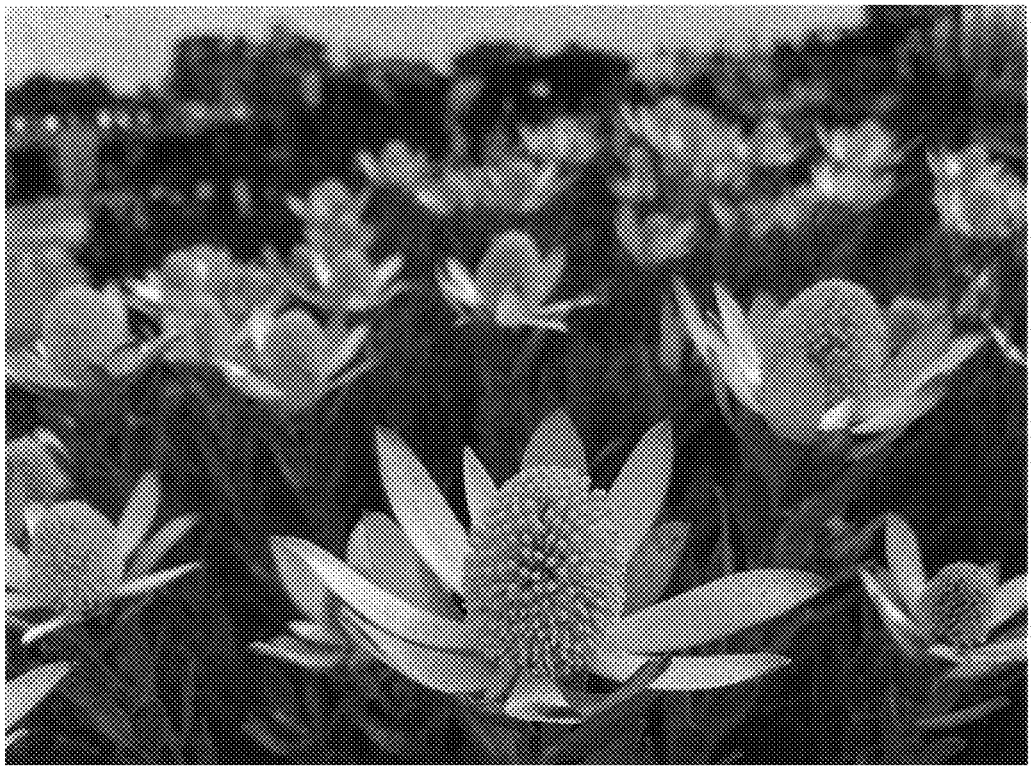

FIG. 2 depicts a close up view of the terminal shoot growth of 'Hawaii Sunrise', and newly-emerged male flowers in mid-late March.

BOTANICAL DESCRIPTION OF THE PLANT

The following is a detailed botanical description of the *Leucadendron* plant named 'Hawaii Sunrise'. Data was collected from a four year old plant which had been grown outdoors in a 5 gallon container in Oxnard, Calif. Phenotypic differences may be observed with variation in environmental, climatic, and cultural conditions. The color determinations are in accordance with the 2007 Edition of The Royal Horticulture Society Colour Chart except where general color terms of ordinary dictionary significance are used.

Botanical classification:

*Family*.—Proteaceae.

*Genus*.—*Leucadendron*.

*Species*.—*stelligerum* x *discolor*.

*Variety*.—'Hawaii Sunrise'.

Parentage:

*Male parent*.—*Leucadendron discolor* (unnamed, unpatented).

*Female parent*.—*Leucadendron stelligerum* (unnamed, unpatented).

Plant description:

*Propagation method*.—Semi-ripe tip cuttings.

*Rooting system*.—Fine and fibrous.

*Vigor*.—Moderate.

*Time to develop roots*.—4 to 6 weeks are needed for a cutting to develop roots at recommended rooting temperature of 20° to 22° Centigrade.

*Crop time*.—Two years are required to produce a full and branched 2-gallon container plant.

*Use*.—Ornamental for use as a landscape plant or container plant.

*Type*.—Perennial in USDA Hardiness Zone 8 and higher.

*Overall dimensions* (*four year old plant in* 5 *gallon container*).—65 cm in height and 65 cm in width.

*Cultural requirements*.—Grow in full sun with moderate water, and well-draining soil.

*Hardiness*.—USDA Zone 8.

*Growth habit*.—Freely branching bush.

*Blooming season*.—Male flowers only are produced with first buds appearing in late January and fully developed flowers by late March.

*Lastingness of blooms*.—4 weeks.

Stem (below first pinch):

*Length*.—8 cm.

*Diameter*.—3 cm to 4 cm.

*Color*.—N200C.

*Shape*.—Coarsely cylindrical.

*Texture*.—Lignified, rough with raised (1.5 mm) ovate lenticels, 3 mm in length, 1.5 mm in width, smooth, color 166B.

Branches (above first pinch):

*Quantity*.—5 to 6 branches.

*Branch length*.—40 cm to 55 cm.

*Internode length*.—6 mm to 8 mm.

*Branch stem diameter*.—6 mm to 8 mm.

*Branch stem shape*.—Cylindrical.

*Branch stem color*.—166B, with paper-like peeling bark, color 156D.

Branches (current year's extension growth):

*Quantity*.—8 to 12 current year branches produced on previous year's wood.

*Branch length*.—10 cm to 15 cm.

*Internode length*.—6 mm.

*Branch stem diameter*.—3 mm.

*Branch stem shape*.—Cylindrical.

*Branch stem color*.—Initially 151D becoming 46A.

Leaves:

*Type*.—Simple.

*Arrangement*.—Slightly offset opposite pairs. Offset distance 2 mm to 3 mm. Distance between pairs (internode distance) 6 mm.

*Attachment*.—Sessile.

*Quantity per branch*.—7 to 9 pairs.

*Shape*.—Oblanceolate.

*Length*.—30 mm to 35 mm.

*Width*.—10 mm.

*Margin*.—Smooth, entire.

*Thickness*.—Slightly fleshy.

*Venation*.—Pinnate but very faint, color as leaf.

*Surface texture*.—Smooth, leathery.

*Color*.—137C except apex and adjacent margin 180A. Apex and margin coloration increases in direct sun and in dry conditions.

*Apex*.—Acute.

*Base*.—Cuneate.

*Fragrance*.—Absent.

Peduncle:

*Length*.—4 mm to 5 mm.

*Shape*.—Cylindrical.

*Diameter*.—3 mm.

*Texture*.—Smooth, semi-glossy.

*Color*.—8B with longitudinal streaks 61B.

Inflorescence and flowers:

*Inflorescence rarely produced until second or third growing season*.

*Inflorescence type*.—Terminal, consisting of dense cluster of male flowers.

*Inflorescence shape*.—Obconical, rounded at apex, flattened at base.

*Inflorescence dimensions*.—Height 2 cm, diameter 1 cm.

*Flowers*.—Quantity: Between 600 and 700 solitary flowers per inflorescence. Arrangement: Solitary flowers, tightly packed in cross-diagonal rows, borne on very short pedicels. Pedicel dimensions: 3 mm in length, approximately 0.75 mm in diameter. Pedicel color: 17B. Development of Flowers: Flowers first open at base of inflorescence. Final flowers open at apex of inflorescence approximately one week later. Fragrance: Absent. Persistent or self-cleaning: Persistent. Flower longevity on the plant: Less than one day in color, two to three weeks while persistent.

Flower color: 17B. Flower basal bracts: 12 to 16 in number, irregularly deltoid, 2.5 mm in length, 1.5 mm in width, color dark purple to black, between 187A and N186A.

Buds:

*Number of buds per inflorescence*.—Between 600 and 700.

*Shape*.—Tetragonal.

*Dimensions*.—0.5 mm to 0.75 mm in height and width.

*Color*.—17B.

Petals:

*Number, arrangement*.—Four, fused at base.

*Shape*.—Oblanceolate.

*Margin*.—Smooth.

*Base*.—Cuneate.

*Apex*.—Acute.

*Dimensions*.—2 mm in length, 0.5 mm to 1.0 mm in width.

*Texture* (*both surfaces*).—Smooth, glabrous.

*Color* (*both surfaces*).—17B.

Involucral bracts:

*Arrangement, number*.—Double whorl consisting of 4 lower bracts and 4 immediately adjacent upper bracts. Occasional single malformed bracts between inflorescence and upper whorl.

*Bract shape*.—Oblanceolate.

*Bract dimensions* (*upper whorl*).—30 mm in length, 7 mm in width.

*Bract dimensions* (*lower whorl*).—35 mm in length, 10 mm in width.

*Margin*.—Smooth, entire.

*Base*.—Truncate.

*Apex*.—Acute.

*Texture*.—Smooth, leathery.

*Bract color* (*both surfaces*).—Ranges between cream 18D (upper whorl) and cream-green 154D (closest match, lower whorl). All bracts colored bright orange-red 33A at apex and apex-adjacent margin, often extending up to 2 mm to 4 mm inward from the margin.

Reproductive organs and seed: None observed.

Drought tolerance: Drought tolerant.

Diseases and pests: 'Hawaii Sunrise' has not been found susceptible or resistant to any particular horticultural pests or diseases.

COMPARISON WITH PARENTAL LINES AND KNOWN VARIETY

'Hawaii Sunrise' differs from the male parent *Leucadendron discolor* by foliage and stem color and by overall size. Whereas 'Hawaii Sunrise' exhibits bright red stems and leaf colors which range from green to plum, the male parent *Leucadendron discolor* bears green leaves on green stems. In addition, whereas 'Hawaii Sunrise' grows to 65 cm in height and 65 cm in width, the male parent *Leucadendron discolor* grows to 2 m to 2.5 m in height and 1.5 m in width.

'Hawaii Sunrise' differs from the female parent *Leucadendron stelligerum* by foliage color and plant size. Whereas 'Hawaii Sunrise' bears green foliage, the leaves of the female parent *Leucadendron stelligerum* are yellow and red in color. In addition, whereas 'Hawaii Sunrise' grows to 65 cm in height and 65 cm in width, the female parent *Leucadendron stelligerum* grows to 1.5 m in height and 1 m in width.

'Hawaii Sunrise' may also be compared with the inventor's variety of *Leucadendron* Plant Named 'Hawaii Magic' (U.S. Plant Pat. No. 29,636). Whereas 'Hawaii Magic' exhibits dramatic foliage color changes during the season, from green to orange-red to plum, plants of 'Hawaii Sunrise' exhibit green foliage with many more current year branches and therefore terminal inflorescences.

I claim:

1. A new and distinct cultivar of *Leucadendron* plant named 'Hawaii Sunrise' as described and illustrated herein.

* * * * *